United States Patent [19]

Satoh et al.

[11] Patent Number: 5,004,742

[45] Date of Patent: Apr. 2, 1991

[54] BENZOTHIAZINE-1,1-DIOXIDE DERIVATIVES

[75] Inventors: Toshio Satoh; Yasunori Niiro; Hisao Kakegawa; Hitoshi Matsumoto, all of Tokushima, Japan

[73] Assignee: Nippon Hypox Laboratories Incorporated, Tokyo, Japan

[21] Appl. No.: 392,899

[22] Filed: Aug. 14, 1989

[51] Int. Cl.$^5$ ..................... A61K 31/54; C07D 279/02
[52] U.S. Cl. .................................. 514/226.5; 544/49
[58] Field of Search ..................... 544/49; 514/226.5

[56] References Cited

U.S. PATENT DOCUMENTS

| | | | |
|---|---|---|---|
| 3,646,020 | 2/1972 | Zinnes et al. | 544/49 |
| 3,853,862 | 12/1974 | Lombardino | 544/49 |
| 3,900,470 | 8/1975 | Rasmussen | 544/49 |
| 3,923,801 | 12/1975 | Rasmussen | 544/49 |
| 3,927,002 | 12/1975 | Lombardino | 544/49 |

*Primary Examiner*—John M. Ford
*Attorney, Agent, or Firm*—Nixon & Vanderhye

[57] ABSTRACT

The present invention relates to novel benzothiazine-1,1-dioxide derivatives. These benzothiazine-1,1-dioxide derivatives have a high hyaluronidase-inhibiting activity and accordingly can be used in drugs such as anti-inflammatory agent, anti-allergic agent and the like.

6 Claims, 2 Drawing Sheets

BENZOTHIAZINE-1,1-DIOXIDE DERIVATIVES

BACKGROUND OF THE INVENTION (1) Field of the Invention

The present invention relates to novel benzothiazine-1,1-dioxide derivatives having an excellent pharmacological action, a process for producing said derivatives, and pharmaceutical compositions comprising said derivatives.

(2) Description of the Prior Art

Various types of anti-inflammatory agents have heretofore been proposed and clinically used. Of them, man in number and typical are adrenocortical steroid-like compounds and cyclooxygenase-inhibiting substances, and these compounds and substances suppress inflammation, i.e. inflammatory edema induced by vasodilation and increased capillary permeability, irrespective of the causes.

However, the adrenocortical steroid-like compounds show adrenal dyscorticism induced by abnormal physiological disturbances, and the cyclooxygenase-inhibiting substances show gastropathy due to the suppression of biosynthesis of gastric mucosa-protecting substance (e.g. prostaglandin $E_2$) as well as a strong adverse effect deviated from this general drug effect.

SUMMARY OF THE INVENTION

Hence, it is an object of the present invention to provide a novel compound which has an anti-inflammatory action, etc. without showing adverse effects (dyscorticism, gastropathy, etc.) as seen in the conventionally used adrenocortical steroid-like compounds and simple cyclooxygenase-inhibiting substances.

The present inventors had previously reported that hyaluronidase takes part in inflammation and allergy, and hyaluronidase-inhibiting agents have a possible anti-inflammatory and anti-allergic activities [Japanese Journal of Inflammation, Vol. 4 No. 4, p. 437 (1984)]. As a result of further study on this matter, the present inventors found that particular benzothiazine-1,1-dioxide derivatives have a strong inhibitory action on hyaluronidase and accordingly are useful as drugs such as anti-inflammatory agent, anti-allergic agent and the like.

Accordingly, the present invention relates to benzothiazine-1,1-dioxide derivatives represented by the general formula (I):

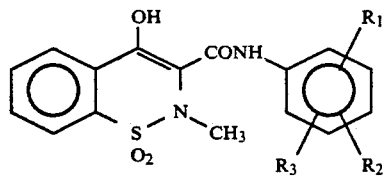

and/or the general formula (II):

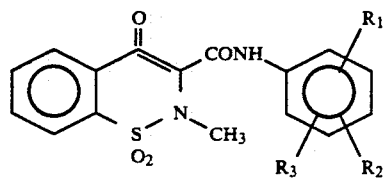

(in the formulas (I) and (II), $R_1$ is a carboxyl group or a tetrazoyl group, and $R_2$ and $R_3$, which can be the same or different, are each an atom or substituent selected from the group consisting of a hydrogen atom, a halogen atom, a hydroxyl group, a nitro group, a cyano group, a trifluoromethyl group, a mercapto group, a lower alkyl group, a lower alkoxy group, a lower alkylcarbonyl group, a lower alkylcarbonyloxy group and a lower thioalkoxy group), or pharmacologically acceptable salts thereof.

The present invention further relates to a process for producing a benzothiazine-1,1-dioxide derivative represented by the above mentioned general formula (I) and/or (II) or a pharmacologically acceptable salt thereof, which process comprises a step of condensing 4-hydroxy-2-methyl-2H-1,2-benzothiazine-1,1-dioxide-3-carboxylic acid or a derivative thereof represented by the general formula (III):

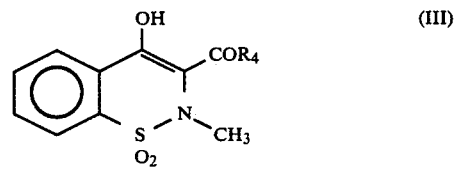

(in the formula (III), $R_4$ is an atom or substituent selected from the group consisting of a hydroxyl group, an alkoxy group, an aryloxy group, an N-oxysuccinimido group, a halogen atom and a group capable of forming an acid anhydride with a neighboring carbonyl (CO) group], with an aniline derivative represented by the general formula (IV):

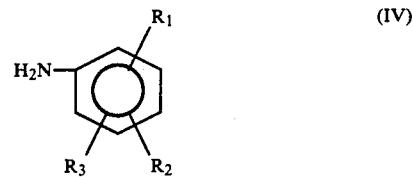

[in the formula (IV), $R_1$ is a carboxyl group or a tetrazoyl group, and $R_2$ and $R_3$, which may be the same or different, are an atom or substituent selected from the group consisting of a hydrogen atom, a halogen atom, a hydroxyl group, a nitro group, a cyano group, a trifluoromethyl group, a mercapto group, a lower alkyl group, a lower alkoxy group, a lower alkylcarbonyl group, a lower alkylcarbonyloxy group and a lower thioalkoxy group] in an inert solvent.

The present invention furthermore relates to pharmaceutical compositions comprising, as an active ingredient, a benzothiazine-1,1-dioxide derivative represented by the above mentioned general formula (I) and/or (II) and/or a pharmacologically acceptable salt thereof, and having a hyaluronidase-inhibiting activity.

DETAILED DESCRIPTION OF THE INVENTION

Figure 1:
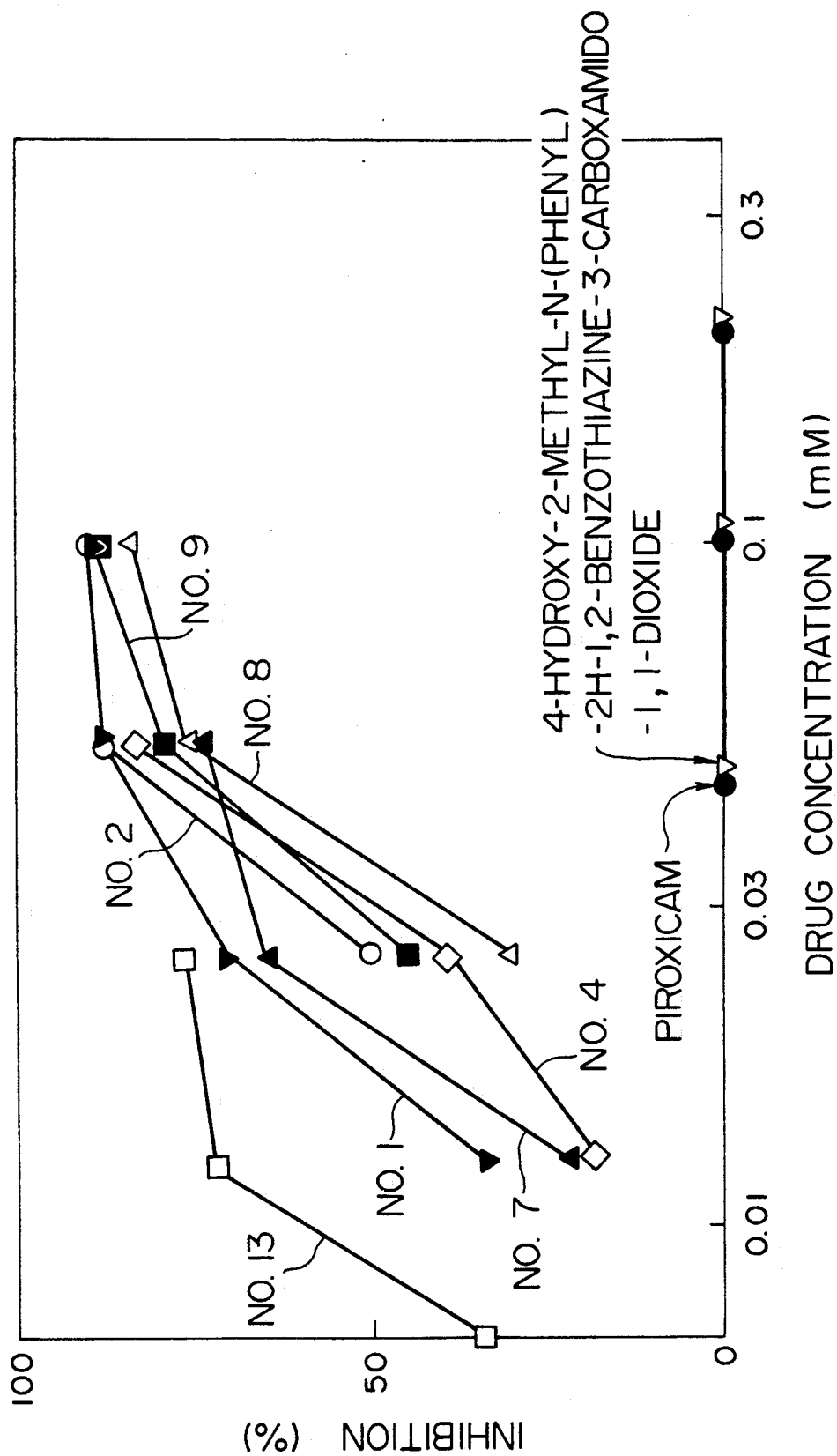
FIG. 1 is a graph showing the hyaluronidase-inhibiting actions of compounds according to the present invention.

Firstly, detailed description is made on the benzothiazine-1,1-dioxide derivative which is the novel compound of the present invention.

As mentioned above, the compound is represented by the general formula (I):

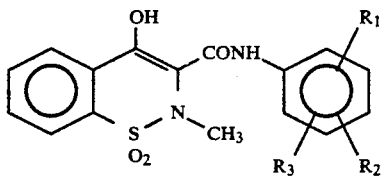

and/or the general formula (II):

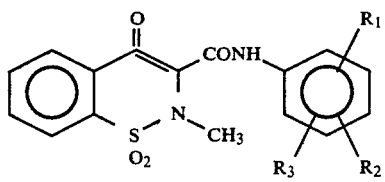

The compound of the present invention is defined by these two general formulas because the compound ordinarily consists of two tautomers represented by the general formulas (I) and (II). Besides the mixture of these two tautomers represented by the general formulas (I) and (II), the compound may further be a single compound represented by the general formula (I) or (II) isolated from the mixture.

The compound of the present invention also includes a pharmacologically acceptable salt obtained from the compound of the general formula (I) and/or the compound of the general formula (II) by a conventional method. As specific examples of the pharmacologically acceptable salt, there can be addition salts of inorganic salts such as sodium salt, potassium salt and the like.

With respect to the substituents in the general formulas (I) and (II), $R_1$ is restricted to a carboxyl group or a tetrazoyl group. The reason is that as is clear from Examples which follow, the compound of the general formula (I) and/or (II) exerts a hyaluronidase-inhibiting action only when $R_1$ is a carboxyl group or a tetrazoyl group.

$R_2$ and $R_3$ may be the same or different and can each take one of the various substituents defined above. The "lower alkyl" in the above definition denotes an alkyl group represented by the general formula $C_nH_{2n+1}$—(n=1-6) of straight chain or branched chain with 1-6 carbon atoms. The "lower alkoxy" denotes an alkoxy group represented by the general formula $C_nH_{2n+1}O$—(n=1-6) of straight chain or branched chain with 1-6 carbon atoms.

The compound of the present invention having a strong inhibitory action against inflammatory enzyme and hyaluronidase is useful for relaxation of the pain caused by disorders such as immediate type allergy, arthritis, rheumatic arthritis and the like and other inflammatory diseases, and accordingly is an effective drug.

When $R_1$ in the compound of the present invention represented by the general formula (I) and/or the general formula (II) is replaced with alkoxycarbonyl group, this ester may also have the same activity since it can be hydrolyzed in vivo to exert the drug effect.

Description is made on the process of the present invention for producing a benzothiazine-1,1-dioxide derivative or a salt thereof.

In the production process of the present invention, there are used, as starting materials, 4-hydroxy-2-methyl-2H-1,2-benzothiazine-1,1-dioxide-3- carboxylic acid or a derivative thereof represented by the general formula (III):

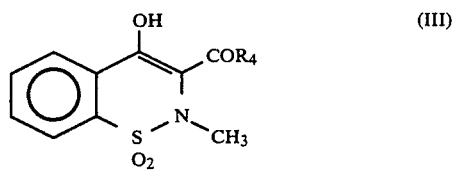

[in the formula (III), $R_4$ is an atom or substituent selected from the group consisting of a hydroxyl group, an alkoxy group, an aryloxy group, an N-oxysuccinimido group, a halogen atom and a group capable of forming an acid anhydride with a neighboring carbonyl (CO) group] and an aniline derivative represented by the general formula (IV):

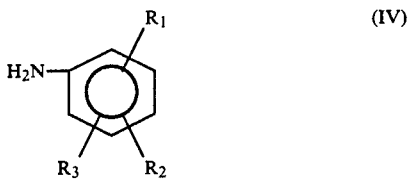

[in the formula (IV), $R_1$ is a carboxyl group or a tetrazoyl group, and $R_2$ and $R_3$, which can be the same or different, are an atom or substituent selected from the group consisting of a hydrogen atom, a halogen atom, a hydroxyl group, a nitro group, a cyano group, a trifluoromethyl group, a mercapto group, a lower alkyl group, a lower alkoxy group, a lower alkylcarbonyl group, a lower alkylcarbonyloxy group and a lower thioalkyoxy group].

The starting material of the general formula (III) is obtained by a known method, for example, a method described in J. Med. Chem. Vol. 14, 1171 (1971). With respect to the $R_4$ in the general formula (III), the alkoxy group is preferably a straight chain or branched chain alkoxy group of 1-6 carbon atoms; the halogen atom is preferably a chlorine atom, an iodine atom or a bromine atom; the aryloxy group is preferably a phenoxy group, a mono-, di- or trinitrophenoxy group or the like.

With respect to the compound of the general formula (IV) as another starting material, some of such compounds are available commercially, and others can be synthesized by a known method.

In order to provide the objective compound of the general formula (I) and the objective compound of the general formula (II) with hyaluronidase-inhibiting activity, it is necessary to use the starting compound of the general formula (IV) wherein $R_1$ is a carboxyl group or a tetrazoyl group, i.e. an aminobenzoic acid derivative or a (tetrazo-5-yl)aniline.

The reaction of the compound of the general formula (III) with the compound of the general formula (IV) is effected in an inert solvent. As the inert solvent, there are preferably used, for example, one or more aromatic hydrocarbon solvents such as dry benzene, toluene, xylene and the like. Other proper organic solvents ma also be used. The compound of the general formula (III) and the compound of the general formula (IV) are used in proportions of preferably 1 mole and 0.1–10 moles, more preferably 1 mole and 0.5–2.5 moles, respectively. By reacting them in said solvent, there takes place a condensation reaction such as dehydration, alcohol removal or dehydrohalogenation, and thereby an objective compound of the general formula (I) and/or an objective compound of the general formula (II) can be obtained. When the condensation reaction gives a volatile alcohol as a by-product, the reaction mixture is subjected to distillation when hot, so as to distil off the alcohol and thereby an objective compound can be easily isolated as a residue.

When it is difficult to distil off the by-produced alcohol, the objective compound can be isolated and purified by a column chromatography which is used in synthetic chemistry, for example, a column chromatography using a silica gel, activated carbon, a polyamide, cellulose or the like.

The objective compound can also be obtained by subjecting the compound of the general formula (III) and the compound of the general formula (IV) to a condensation reaction with a condensing agent such as dicyclohexylcarbodiimide or the like. The objective compound can also be obtained by other condensation reaction which is useful in organic synthesis, such as an acid anhydride method, an acid halide method, a phosphazo method or the like.

Then, description is made on the pharmaceutical composition of the present invention.

The pharmaceutical composition of the present invention is characterized by comprising, as an active ingredient, a benzothiazine-1,1-dioxide derivative represented by the general formula (I) and/or the general formula (II) and/or a pharmacologically acceptable salt thereof, and having a hyaluronidase-inhibiting activity. As mentioned above, this hyaluronidase-inhibiting activity is expressed when the substituent $R_1$ in the compound of the general formula (I) and/or the general formula (II) is a carboxyl group or a tetrazoyl group. Thus, the pharmaceutical composition of the present invention comprises an active ingredient having a hyaluronidase-inhibiting activity and is effective for relaxation of the pain caused by diseases such as immediate type allergy, arthritis, rheumatic arthritis and the like and other inflammatory diseases.

When the pharmaceutical composition of the present invention is administered to patients with the above diseases as a remedy, the dose has no particular restriction and varies depending upon the type of diseases, the disease conditions, age, health condition and body weight of patient, the frequency of administration, the expected effect and the type of the concurrently prescribed drug, if any. However, the dose is about 5–1,000 mg, preferably about 10–500 mg in terms of active ingredient, per adult per day, and it is administered orally or parenterally one or more times per day. When the pharmaceutical composition of the present invention is used as a remedy particularly for various inflammatory diseases or allergic diseases, the dose is within the above range. Ordinarily, however, the dose is preferably about 10–500 mg, more preferably about 30–300 mg per adult per day.

As the dosage form, there can be mentioned, for example, powders, parvules, granules, tablets, capsules, suppositories, injections, etc. These dosage forms can be prepared using ordinary vehicles, adjuvants, additives and the like by an ordinary method.

That is, when a solid form for oral administration is prepared, the active ingredient is mixed with vehicles and, if necessary, binders, disintegrants, lubricants, colorants, flavoring substances, etc. and the mixture is made into tablets, coated tablets, granules, powders, capsules or the like by an ordinary method.

As the vehicle, there are, for example, lactose, corn starch, white sugar, glucose, sorbitol, crystalline cellulose, silicon dioxide and the like; as the binder, there are, for example, a polyvinyl alcohol, a polyvinyl ether, ethyl cellulose, methyl cellulose, gum arabic, tragacanth gum, gelatin, shellac, hydroxypropyl cellulose, hydroxypropyl starch, polyvinyl pyrrolidone and the like; as the disintegrant, there are used, for example, starch, agar, a gelatin powder, crystalline cellulose, calcium carbonate, sodium hydrogencarbonate, calcium citrate, dextrine, pectin and the like; as the lubricant, there are used, for example, magnesium stearate, talc, a polyethylene glycol, silica, a hardened vegetable oil and the like; as the colorant, there can be used those officially allowed substances only for use in drugs; and as the flavorings, there are used a cocoa powder, menthol, aromatic acid(s), peppermint oil, borneol, a cinnamon powder and the like. If necessary, the tablets and granules may be coated with sugar, gelatin or other appropriate coating material.

When injections are prepared, the active ingredient is mixed with a pH-adjusting agent, a buffering agent, a stabilizer, a solubilizer, etc. if necessary, and the mixture is made into intravenous injections by an ordinary method.

EXAMPLES

Next, Examples of the present invention are described.

Synthesis Example 1

To 6.0 g of a compound of the formula (III), i.e. 4-hydroxy-2-methyl-3-methoxycarbonyl-2H-,1,2-benzothiazine-1,1-dioxide was added 3.8 g of a compound of the formula (IV), i.e. 2-(tetrazo-5'-yl)aniline. The mixture was refluxed for 24 hours in 80 ml of o-xylene to effect a condensation reaction.

The insoluble materials were collected by filtration while the reaction mixture was hot, followed by washing with o-xylene. The residue was recrystallized from dioxane-water to obtain 7.5 g of 4-hydroxy-2-methyl-N-[2'-(tetrazo-5''-yl)phenyl]-2H-1,2-benzothiazine-3-carboxamido-1,1-dioxide (this corresponds to the compound No. 1 in Table 1).

Melting point: 256–258° C.
Elemental analysis (wt. %)
Calculated for $C_{17}H_{14}N_6O_4$: C 52.25, H 3.54.
Found: C 51.30, H 3.56.

Synthesis Examples 2–15

The following benzothiazine-1,1-dioxide derivatives were obtained by basically the same procedure as described in Synthesis Example 1 except that various aniline derivatives different from that of Synthesis Example 1 were used as a compound of the formula (IV).

| Compound No. | Name of compound |
|---|---|
| 2 | 4-Hydroxy-2-methyl-N-(2'-carboxyphenyl)-2H-1,2-benzothiazine-3-carboxamido-1,1-dioxide |
| 3 | 4-Hydroxy-2-methyl-N-(2'-carboxy-4'-chlorophenyl)-2H-1,2-benzothiazine-3-carboxamido-1,1-dioxide |
| 4 | 4-Hydroxy-2-methyl-N-(2'-carboxy-5'-chlorophenyl)-2H-1,2-benzothiazine-3-carboxamido-1,1-dioxide |
| 5 | 4-Hydroxy-2-methyl-N-(2'-carboxy-3'-methylphenyl)-2H-1,2-benzothiazine-3-carboxamido-1,1-dioxide |
| 6 | 4-Hydroxy-2-methyl-N-(2'-carboxy-4'-methylphenyl)-2H-1,2-benzothiazine-3-carboxamido-1,1-dioxide |
| 7 | 4-Hydroxy-2-methyl-N-(2'-carboxy-4'-hydroxyphenyl)-2H-1,2-benzothiazine-3-carboxamido-1,1-dioxide |
| 8 | 4-Hydroxy-2-methyl-N-(2'-carboxy-6'-hydroxyphenyl)-2H-1,2-benzothiazine-3-carboxamido-1,1-dioxide |
| 9 | 4-Hydroxy-2-methyl-N-(2'-carboxy-5'-nitrophenyl)-2H-1,2-benzothiazine-3-carboxamido-1,1-dioxide |
| 10 | 4-Hydroxy-2-methyl-N-(3'-carboxyphenyl)-2H-1,2-benzothiazine-3-carboxamido-1,1-dioxide |
| 11 | 4-Hydroxy-2-methyl-N-(4'-carboxyphenyl)-2H-1,2-benzothiazine-3-carboxamido-1,1-dioxide |
| 12 | 4-Hydroxy-2-methyl-N-(3'-carboxy-6'-chlorophenyl)-2H-1,2-benzothiazine-3-carboxamido-1,1-dioxide |
| 13 | 4-Hydroxy-2-methyl-N-(3'-carboxy-2'-hydroxyphenyl)-2H-1,2-benzothiazine-3-carboxamido-1,1-dioxide |
| 14 | 4-Hydroxy-2-methyl-N-(3'-carboxy-4'-hydroxyphenyl)-2H-1,2-benzothiazine-3-carboxamido-1,1-dioxide |
| 15 | 4-Hydroxy-2-methyl-N-(4'-carboxy-5'-hydroxyphenyl)-2H-1,2-benzothiazine-3-carboxamido-1,1-dioxide |

The melting points and mass spectral data of the above obtained compound Nos. 2–15 are shown in Table 1, together with those of the compound No. 1 obtained in Synthesis Example 1.

TABLE 1

| No. | $R_1$ | $R_2$ | $R_3$ | Yield (%) | m.p. (°C.) | MS (m/e) |
|---|---|---|---|---|---|---|
| 1 | 2'-(tetrazo-5"-yl) | H | H | 84 | 256–258 | 398 |
| 2 | 2'-COOH | H | H | 78 | 259–262 | 374 |
| 3 | 2'-COOH | 4'-Cl | H | 76 | 262–265 | 408 |
| 4 | 2'-COOH | 5'-Cl | H | 65 | 264–268 | 408 |
| 5 | 2'-COOH | 3'-CH$_3$ | H | 52 | 210–213 | 388 |
| 6 | 2'-COOH | 4'-CH$_3$ | H | 84 | 228–235 | 388 |
| 7 | 2'-COOH | 4'-OH | H | 31 | 289–291 | 372 (M$^+$—H$_2$O) |
| 8 | 2'-COOH | 6'-OH | H | 43 | 251–255 | 390 |
| 9 | 2'-COOH | 5'-NO$_2$ | H | 69 | 284–288 | 419 |
| 10 | 3'-COOH | H | H | 93 | 289–298 | 374 |
| 11 | 4'-COOH | H | H | 86 | >290 | 374 |
| 12 | 3'-COOH | 6'-Cl | H | 95 | 282–286 | 408 |
| 13 | 3'-COOH | 2'-OH | H | 91 | 273–275 | 390 |
| 14 | 3'-COOH | 4'-OH | H | 60 | 275–278 | 390 |
| 15 | 4'-COOH | 5'-OH | H | 41 | 238–241 | 390 |

Next, the pharmacological actions of the compound of the present invention are described by way of Pharmacological Tests.

Pharmacological Test 1

Effect on hyaluronidase activity 0.8 mg/ml of a hyaluronidase (a product of Sigma Co.) taken from bovine testicles was used as an enzyme. Test compounds (compound Nos. 1, 2, 4, 7, 8, 9 and 13) were dissolved at various concentrations in a 1 M acetate buffer (pH 3.5) and heated at 37° C. for 20 minutes. Then, calcium chloride was added to each of the resulting solutions so that the calcium chloride concentration became 5 mM, and each of the resulting mixtures was heated at 37° C. for 20 minutes.

Thereto was added potassium hyaluronate so that its concentration in the buffer became 2.4 mg/ml, and the mixture was heated at 37° C. for 40 minutes.

After the termination of the reaction, the amount of the substrate hydrolyzed was determined at 585 nm using the Elson-Morgan's procedure, from which there were determined the effects of each test compound at various concentrations on the normal enzymatic reaction.

The results are shown in FIG. 1. The solid circles along the ordinate indicate piroxicam, and the open deltas indicate 4-hydroxy-2-methyl-N-(phenyl)-2H-1,2-benzothiazine-3-carboxamido-1,1-dioxane as discussed below.

It has become clear from the results of FIG. 1 that the compound of the present invention has an excellent inhibitory action against hyaluronidase.

In this test, there was also examined Piroxicam which is an inhibitor for cyclooxygenase. Although this drug belongs to benzothiazine-1,1-dioxide derivatives, it showed no effect on hyaluronidase activity at a concentration range of 0.01–0.3 mM employed in the test. Further, 4-hydroxy-2-methyl-N-(phenyl)-2H-1,2-benzothiazine-3-carboxamido-1,1-dioxide showed no effect either in the same concentration range.

It has become clear from this test that the $R_1$ of the benzothiazine-1,1-dioxide derivative represented by the general formula (I) and/or the general formula (II) must be a carboxyl group or a tetrazoyl group in order for the derivative to show a hyaluronidase-inhibiting action.

It has also become clear that the hyaluronidase-inhibiting activity of the present compound is very high considering that the "50% enzyme inhibition" concentration of Tranilast [which is an anti-allergic agent and also a hyaluronidase-inhibiting agent reported by the present inventors in Chem. Pharm. Bull., 33 (9), 3738 (1985)] is about 0.23 mM.

Pharmacological Test 2

Action against rat plantar edema induced by carrageenin

Figure 2:
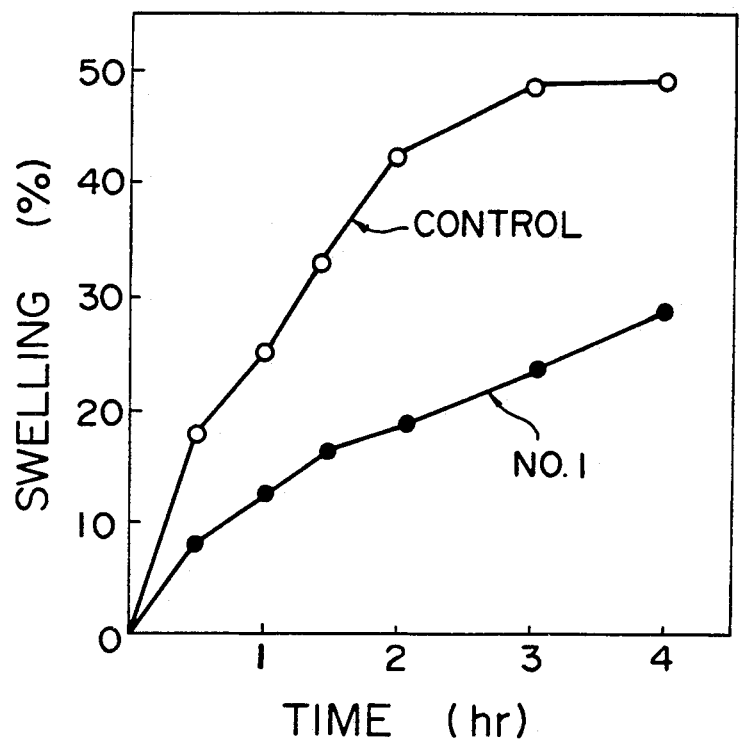
FIG. 2 is a graph showing the effect of a compound according to the present invention on the rat plantar edema induced by carrageenin.

Male Sprague-Dawley rats weighing 200–250 g were injected s.c. (subcutaneously) with 0.1 ml of carrageenin into the subplantar region of the right hind paw. 60 minutes before the carrageenin administration, a test compound (compound No. 1) had been administered p.o. (orally). The compound No. 1 showed a noticeably high inhibitory action against edema in an administration amount of 200 mg per kg of rat body weight, as compared with the control where only the carrageenin solution was administered. That is, as shown in FIG. 2, in 30 minutes after the carrageenin administration, the swelling percent is 8.0% in the compound No. 1, while it is 18.2% in the control. Therefore, the inhibition of the compound No. 1 reached 54% in 30 minutes after the carrageenin administration. About the same inhibition (%) was seen also in 1, 1.5, 2 and 3 hours after the carrageenin administration. Thus, the anti-inflammatory effect of the compound of the present invention was proven in this animal test.

Pharmacological Test 3

Action on histamine liberation from fat peritoneal mast cells by concanavalin A

This test was effected in accordance with the method of R. P. Siraganian [J. Immunol., 114, 886 (1974)]. That is, a Locke solution containing phosphatidylserine, a test compound and a suspension of rat peritoneal mast cells was heated for 20 minutes at 37° C. Incidentally, the concentrations of phosphatidylserine and the test compound in the Locke solution were 3.0 μg/ml and 0.2 mM, respectively. A concanavalin A solution was added to the Locke solution, and the mixture was subjected to a reaction for 10 minutes at 37° C. After ice-cooling, the reaction mixture was subjected to centrifugation for 10 minutes at 4° C. Both the supernatant and the precipitate were measured for histamine content by the method of Shore et al. [J. Exp. Ther., 127, 182 (1959)] to determine a ratio of histamine liberated. The results are shown in Table 2. As seen in Table 2, the compounds of the present invention showed an inhibitory action against the normal histamine liberation reaction without using any test compound.

The present inventors had previously reported that known anti-allergic agents, for example, Tranilast shows, at 0.3 mM, an inhibition of about 20% in the same reaction of histamine liberation from rat peritoneal mast cells by concanavalin A and thereby expresses an anti-allergic action [Chem. Pharm. Bull., 33 (9), 3738 (1985)]. As compared with that of Tranilast, the tested compounds of the present invention definitely show a very high activity, and this activity can lead to suppress allergic reaction effectively.

Pharmacological Test 4

Action on rat 48-hour homologous PCA reaction

Male SD rats weighing 200-250 g were injected with 0.1 ml of a rat anti-egg albumin serum diluted with a physiological saline solution, intradermally at the back in order to passively sensitize the rats. After 48 hours, 0.5 ml of 1% Evans Blue containing 5 mg of antigen (egg albumin) was administered intravenously. After 30 minutes, each rat was sacrificed by bleeding and the skin was peeled off. Then, the amount of the coloring material in the lesion was determined by the method of Katayama et al. [Microbial. Immunol., 122 (2), 89 (1987)]. Incidentally, each test compound had been administered orally 60 minutes before the antigen administration.

The results are shown in Table 3.

The compound No. 1 of the present invention showed a higher suppressive action than the control (Tranilast).

Thus, the anti-allergic action of the compound of the present invention was proven in this animal test.

Pharmacological Test 5

Action on gastropathy

The compound No. 1 of the present invention and two known cyclooxygenase inhibitors, i.e. Indometacin and Piroxicam were examined for action on rat gastric mucosa. That is, the compound No. 1, Indometacin or Piroxicam was administered orally to male SD rats (body weight: 200-250 g) which had been fasted for 24 hours. After the administration, the rats were allowed to no food and no water for 48 hours. Then, the stomach of each rat was removed under ether anesthesia and fixed with formalin. The resulting stomach was incised and the length of the mucous ulcer generated in the glandular portion of the stomach was measured using a dissecting microscope (magnification of 10). The results are shown in Table 4. No ulcer was seen in any of the rats to which the compound No. 1 of the present invention had been administered in an amount of 100, 300 or 500 mg/kg.

Meanwhile, when Piroxicam was administered, all the rats formed severe ulcer in an administration amount of 100 mg/kg, and 3 out of the 5 rats tested died and the surviving 2 rats formed very severe ulcer in an administration amount of 300 mg/kg. When Indometacin was administered, all the rats formed very serious ulcer in an administration amount of 50 mg/kg.

This test proved that the compound of the present invention causes no gastropathy.

TABLE 2

| Test compound | Inhibition (%) | Test compound | Inhibition (%) |
|---|---|---|---|
| No. 1 | 93.9 | No. 7 | 86.0 |
| No. 2 | 81.3 | No. 8 | 83.7 |
| No. 3 | 65.0 | No. 9 | 106.5 |
| No. 4 | 85.1 | No. 10 | 90.7 |
| No. 5 | 85.2 | No. 11 | 60.3 |
| No. 6 | 63.0 | | |

TABLE 3

| Test compound | Amount administered (mg/kg) | Administration route | Amount of colorant which leaked out (μg/site) | Suppression (%) |
|---|---|---|---|---|
| Control | — | p.o. | 9.7 ± 1.9 | — |
| No. 1 | 200 | p.o. | 3.4 ± 1.3 | 65.1 |
| No. 2 | 200 | p.o. | 6.8 ± 2.3 | 29.3 |

TABLE 4

| Test compound | Amount administered (mg/kg) | Administration route | Number of rats in one group | Ulcer index mean S.E. |
|---|---|---|---|---|
| No. 1 | 100 | p.o. | 5 | 0 |
| | 300 | p.o. | 4 | 0 |

TABLE 4-continued

| Test compound | Amount administered (mg/kg) | Administration route | Number of rats in one group | Ulcer index mean S.E. |
|---|---|---|---|---|
| | 500 | p.o. | 5 | 0 |
| Piroxicam | 100 | p.o. | 5 | 14.4 ± 8.0 |
| | 300 | p.o. | 2* | 65.5 ± 33.5 |
| Indometacin | 50 | p.o. | 5 | 42.8 ± 8.7 |

*Ulcer index was determined on 2 surviving rats of the 5 rats tested.

Toxicity Test 1

The compound of the present invention was further tested for acute toxicity by intravenous injection using male ddy mice. There was no death when the compound No. 1 of the present invention was administered in an amount of 10–500 mg/kg (each group consisted of 10 mice).

Thus, the compound of the present invention showed a very strong inhibitory action against hyaluronidase (which is an inflammatory enzyme), and exhibited suppressive effects for edema induced by carrageenin, liberation of histamine from rat peritoneal mast cells by concanavalin A, and rat homologous PCA reaction.

Further, no gastropathy and no substantial adverse effect were seen both macroscopically and microscopically when the compound of the present invention was administered to a test animal in an amount exceeding the level at which the efficacy is expressed.

Therefore, the compound of the present invention is useful as a drug for relaxation of the pain caused by diseases such as arthritis, rheumatic arthritis and the like and other inflammatory diseases and also for relaxation of diseases such as bronchial asthma, nasal allergy and other diseases caused by allergic reaction.

Next, there are shown Preparation Examples of the pharmaceutical composition of the present invention.

Preparation Example 1

Tablets

| | |
|---|---|
| Compound No. 1 of the present invention | 50 g |
| Lactose | 10 g |
| Corn starch | 30 g |
| Crystalline cellulose | 8 g |
| Hydroxypropyl cellulose | 1 g |
| Magnesium stearate | 1 g |
| | 100 g |

Procedure

There was mixed the compound No. 1 of the present invention, lactose, corn starch and crystalline cellulose. Thereto was added a solution of hydroxypropyl cellulose dissolved in 30 mol of water, and the resulting mixture was kneaded thoroughly. The kneaded material was passed through a 20-mesh sieve to obtain granules. The granules were dried and then mixed with magnesium stearate. The mixture was made into tablets each of 100 mg.

Preparation Example 2

Capsules

| | |
|---|---|
| Compound No. 1 of the present invention | 100 g |
| Lactose | 100 g |
| Corn starch | 50 g |
| Crystalline starch | 47 g |
| Magnesium stearate | 3 g |
| | 300 g |

Procedure

The above ingredients were mixed thoroughly and encapsulated by 300-g portions to obtain capsules.

Preparation Example 3

Granules

| | |
|---|---|
| Compound No. 1 of the present invention | 100 g |
| Lactose | 470 g |
| Corn starch | 400 g |
| Hydroxypropyl cellulose | 30 g |
| | 1000 g |

Procedure

There were mixed the compound No. 1 of the present invention, lactose and corn starch. Thereto was added a solution of hydroxypropyl cellulose dissolved in 400 ml of water, and the mixture was kneaded thoroughly. The kneaded material was passed through a 29-mesh sieve to obtain pellets. The pellets were dried and then uniformalized in size to obtain granules.

Preparation Example 4

Suppositories

| | |
|---|---|
| Compound No. 1 of the present invention | 50 g |
| Macrogol 4000 | 200 g |
| Macrogol 1500 | 50 g |
| | 300 g |

Procedure

Macrogols 4000 and 1500 were melted on a water bath. Thereto was added a fine powder of the compound No. 1 of the present invention. The mixture was stirred until the powder was dispersed uniformly. The dispersion was poured into a suppository mold to obtain suppositories.

As described in detail above, there have been provided, according to the present invention, benzothiazine-1,1-dioxide derivatives having a hyaluronidase-inhibiting activity and useful as an active ingredient of drug, as well as a process for producing said derivative.

There have also been provided pharmaceutical compositions comprising the above compounds as an anti-inflammatory agent or an anti-allergic agent.

What is claimed is:

1. A benzothiazine-1,1-dioxide derivative represented by the formula (I):

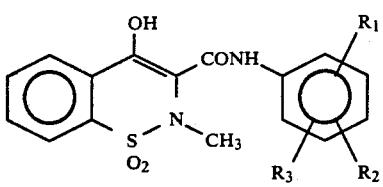 (I)

or the formula (II):

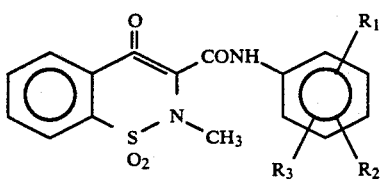 (II)

[in the formulas (I) and (II), $R_1$ is a carboxyl group or a tetrazoyl group, and $R_2$ and $R_3$, which can be the same or different, are each an atom or substituent selected from the group consisting of a hydrogen atom, a halogen atom, a hydroxyl group, a nitro group, a cyano group, a trifluoromethyl group, a mercapto group, a lower alkyl group, a lower alkoxy group, a lower alkylcarbonyl group, a lower alkylcarbonyloxy group and a lower thioalkoxy group], or a pharmacologically acceptable salt thereof.

2. A benzothiazine-1,1- dioxide derivative or a pharmacologically acceptable salt thereof according to claim 1, wherein $R_1$ is a carboxyl group or a tetrazoyl group, $R_2$ is an atom or substituent selected from the group consisting of a hydrogen atom, a halogen atom, a hydroxyl group, a nitro group and a lower alkyl group, and $R_3$ is a hydrogen atom.

3. A pharmaceutical composition comprising, as the active hyaluronidase-inhibiting ingredient, an effective amount of a benzothiazine-1,1-dioxide derivative or a pharmacologically acceptable salt thereof as defined in claim 1 together with a pharmaceutically acceptable carrier or diluent.

4. The pharmaceutical composition of claim 3, containing from 5 to 1,000 mg. of said active ingredient.

5. The pharmaceutical composition of claim 4, containing from 10 to 500 mg. of said active ingredient.

6. The pharmaceutical composition of claim 5, containing from 30 to 300 mg. of said active ingredient.

* * * * *